(12) United States Patent
Wagner (10) Patent No.: US 7,658,884 B2
(45) Date of Patent: Feb. 9, 2010

(54) PHOTOMETRIC METHOD AND APPARATUS FOR MEASURING A LIQUID'S TURBIDITY, FLUORESCENCE, PHOSPHORESCENCE AND/OR ABSORPTION COEFFICIENT

(75) Inventor: Heinz Wagner, Zürich (CH)

(73) Assignee: Swan Analytische Instrumente AG, Riedikon (CH)

( * ) Notice: Subject to any disclaimer, the term of this patent is extended or adjusted under 35 U.S.C. 154(b) by 633 days.

(21) Appl. No.: 11/243,610

(22) Filed: Oct. 5, 2005

(65) Prior Publication Data
US 2007/0077178 A1    Apr. 5, 2007

(51) Int. Cl.
G01N 33/00 (2006.01)
G01N 15/06 (2006.01)
G01N 21/00 (2006.01)
G01N 21/64 (2006.01)
G01N 21/85 (2006.01)

(52) U.S. Cl. .......... 422/68.1; 422/55; 422/58; 422/82.05; 422/82.07; 422/82.08; 250/574; 250/575; 250/576; 356/337; 356/338; 356/339; 356/340

(58) Field of Classification Search .......... None
See application file for complete search history.

(56) References Cited

U.S. PATENT DOCUMENTS 3,065,665 A    11/1962   Mohd et al.

(Continued)

FOREIGN PATENT DOCUMENTS

JP    51 071186 A    6/1976

(Continued)

OTHER PUBLICATIONS

International Search Report and Written Opinion of International Application No. PCT/EP2006/066656.

*Primary Examiner*—Jill Warden
*Assistant Examiner*—Neil Turk
(74) *Attorney, Agent, or Firm*—Notaro & Michalos P.C.

(57) ABSTRACT

The apparatus for deriving at least one property like turbidity or fluorescence of a sample liquid from measuring emitted light emitted from said sample liquid upon irradiation of said sample liquid with a probe light beam comprises a container for containing said sample liquid, said sample liquid forming a sample surface. It furthermore comprises a light source for generating said probe light beam directed, in an angle $\beta1 \neq 0°$ with respect to a sample surface normal, at said sample surface, and a detector adapted to detecting an intensity of said emitted light emitted through said sample surface out of said sample liquid generally along a first detection axis, said first detection axis forming an angle $\gamma1 \neq 0°$ with a sample surface normal. It also comprises an optical barrier arranged between said probe light beam and said first detection axis adapted to blocking a propagation of light originating from reflection or scattering of said probe light beam at said sample surface generally along said first detection axis. The apparatus may comprise an outlet section for removing sample liquid from said container, having at least one opening to said main section located beneath said sample surface and a first separating member for substantially separating a portion of said sample surface belonging to said outlet section from a portion of said sample surface belonging to a main section, where said light enters and exits the sample liquid.

29 Claims, 3 Drawing Sheets

U.S. PATENT DOCUMENTS

| | | | | |
|---|---|---|---|---|
| 3,364,812 A | * | 1/1968 | Ewing | 356/339 |
| 4,943,370 A | | 7/1990 | Gortowski | |
| 5,198,369 A | * | 3/1993 | Itoh et al. | 436/534 |
| 5,940,178 A | * | 8/1999 | Barber et al. | 356/339 |

FOREIGN PATENT DOCUMENTS

| | | |
|---|---|---|
| JP | 3-54436 | 3/1991 |
| RU | 2235310 | 4/2003 |
| WO | WO 02/16917 A | 2/2002 |

\* cited by examiner

PHOTOMETRIC METHOD AND APPARATUS FOR MEASURING A LIQUID'S TURBIDITY, FLUORESCENCE, PHOSPHORESCENCE AND/OR ABSORPTION COEFFICIENT

TECHNICAL FIELD

The invention relates to the field of measuring a liquid's property by measuring light emitted from said liquid, which is excited by a probe light beam. The invention relates in particular to the field of nephelometry and the measurement of turbidity, and to measuring fluorescence and measuring phosphorescence and/or absorption. It relates to a corresponding measuring apparatus, a flow cell for such apparatus, and to a corresponding measuring method.

Such devices and methods find application, e.g., in chemical industry, pharmaceutical industry, semiconductor production, cooling water monitoring, drinking water and ground water analysis and monitoring.

BACKGROUND OF THE INVENTION

In many turbidimeters and nephelometers known in the art a sample is illuminated through a window. A problem occurring through this is, that the window may be contaminated and accordingly loose (some of) its transparency. It is not easy to distinguish the corresponding loss of light intensity from the effect of a different turbidity of the sample.

A free-fall arrangement is also known from the art: a sample liquid forming a free-forming jet is illuminated by light, and scattered light is detected. In such arrangements, windows are not needed, but usually a large amount of sample liquid is needed for measurements.

From U.S. Pat. No. 5,400,137 a photometric means is known, which allows to determine fluorescence and scattering of a sample liquid. Two light beams of different wavelengths are directed at a surface of said sample liquid, and a detector detects light emitted therupon from said sample liquid. The sample surface is formed in a container and its boundary is formed by means of an edge to be overflown by excessive sample liquid.

In RU 2,235,310 a turbidimeter is presented, in which a sample liquid contained in a vessel is illuminated through its surface by light directed parallel to a surface normal of sample surface, i.e., illumination takes place through vertically directed light. Detection of light scattered by the sample liquid also takes place along an axis parallel to a surface normal of the sample surface. Two light emitters are separated from two detectors by vertically aligned opaque partitions having horizontal slots, the slots being arranged within the sample liquid in immediate vicinity of the sample surface. The partitions serve to prevent any repeated reflections from the vessel's bottom and walls. Excess sample liquid overflows an edge of the vessel in immediate vicinity of the spot, at which the light is directed. One problem with such an apparatus is that the intensity of detected light will be very low, since light incidence direction and detection direction are antiparallel to each other. Another problem could be that the sample surface is not very stable because of the close proximity of the overflow-edge and the spot, at which the light is directed. But, according to said RU 2,235,310, any kind of instabilitites do not at all affect the measurement, because measured intensities (of both detectors, upon illumination with each light source) are evaluated in a special way.

In JP 03-54436 a turbidimeter is disclosed, in which polarized light is obliquely directed at the surface of a sample liquid contained in a container. Scattered light thereupon emitted from the sample liquid is detected polarization-sensitively by a detector located outside the sample liquid, the detector comprising a polarizer. Between the sample liquid and said polarizer a cylinder is arranged for intercepting external light. The container has an edge, which is to be overflown by excess sample liquid.

SUMMARY OF THE INVENTION

A goal of the invention is to create an apparatus for deriving at least one property of a sample liquid from measuring emitted light emitted from said sample liquid upon irradiation of said sample liquid with a probe light beam, which has an increased accuracy.

One object of the invention is to provide for such an apparatus, which has an increased measurement stability.

Another object of the invention is to provide for such an apparatus, which is of small dimension.

Another object of the invention is to provide for such an apparatus, which requires only relatively small amounts of sample liquid for measuring.

Another object of the invention is to provide for such an apparatus, which has a short response time.

Another object of the invention is to provide for such an apparatus, which allows for fast and/or time-resolved measurements.

Another object of the invention is to provide for such an apparatus, by means of which an absorption coefficient and, in addition, turbidity or fluorescence or phosphorescence can be derived.

Another object of the invention is to provide for a flow cell for use with such an apparatus.

Another object of the invention is to provide for a corresponding method for deriving at least one property of a sample liquid, which has an increased accuracy.

One object of the invention is to provide for such a method, which has an increased measurement stability.

Another object of the invention is to provide for such a method, which requires only relatively small amounts of sample liquid for measuring.

Another object of the invention is to provide for such a method, which has a short response time.

Another object of the invention is to provide for such a method, which allows for fast and/or time-resolved measurements.

Another object of the invention is to provide for such a method, by means of which an absorption coefficient and, in addition, turbidity or fluorescence or phosphorescence can be derived.

These objects are achieved by an apparatus, a flow cell and by a method, respectively, according to the patent claims.

According to the invention, the apparatus for deriving at least one property of a sample liquid from measuring emitted light emitted from said sample liquid upon irradiation of said sample liquid with a probe light beam, comprises a container for containing said sample liquid, said sample liquid forming a sample surface;

a light source for generating said probe light beam directed, in an angle $\beta1 \neq 0°$ with respect to a surface normal of said sample surface, at said sample surface in a main section of the container;

a first detector adapted to detecting an intensity of said emitted light emitted through said sample surface in said main section out of said sample liquid generally along a first detection axis, said first detection axis forming an angle $\gamma1 \neq 0°$ with a surface normal of said sample surface; and an optical barrier arranged between said probe light beam and said first detection axis adapted to blocking a propagation of light originating from reflection or scattering of said probe light beam at said sample surface generally along said first detection axis.

The apparatus can be considered a photometric means or a photometric apparatus or a measuring or monitoring or analyzing apparatus or means. When a turbidity of said sample liquid is measured, said apparatus can be named a turbidimeter or a nephelometer.

Optical elements like light source and detector and corresponding lenses, beam splitters and the like can be arranged outside from the sample liquid. They are not exposed to sample liquid and are therefore (practically) not subject to contamination. Furthermore, neither the probe light beam nor the emitted light to be detected has to pass a window that would be in contact with sample liquid.

When a probe light beam impinges on a sample surface (at an angle at which no total reflection occurs), it not only continues within the sample liquid as a refracted beam, but it is also reflected and scattered at the sample surface. The intensity of such reflected and such scattered light is often two or three or even more orders of magnitude higher than the intensity of the emitted light to be detected by the detector. The optical barrier avoids, that said reflected or scattered light reaches the detector, so that it is not detected and accordingly does not influence the measurement. It has to be noted that not only the signal-to-noise ratio would otherwise be strongly decreased, but also, that the intensity, in particular of said reflected light, varies strongly, when the sample surface changes slightly, e.g., due to a little wave from some vibration. The measurement stability would be low.

With $\beta1 \neq 0°$ and $\gamma1 \neq 0°$ it is possible to have the probe light beam locally separated from the beam of emitted light to be detected and yet be able to measure emitted light that has undergone no scattering or single scattering only.

It is possible to use a polarized probe light beam or to use an unpolarized probe light beam. It is also possible to use polarization-sensitive detection (e.g., by arranging a polarizer before a photo-sensitive element) or to use a polarization-insensitive detector.

In one embodiment said container comprises
an outlet section for removing sample liquid from said container, having at least one opening to said main section located beneath said sample surface; and
a first separating member for substantially separating a portion of said sample surface belonging to said outlet section from a portion of said sample surface belonging to said main section.

Although an apparatus according to the invention may be, used for off-line analysis, wherein a certain volume of sample liquid is filled into said container and then analyzed (no flow during measurement), but typically, an apparatus according to the invention will be used in-line, i.e., sample liquid flows steadily through said container and is continuously (or in intervals) analyzed. In particular, when used in-line, said first separating member is helpful, because in said outlet section sample liquid is continuously removed from said container. A removal of sample liquid usually leads to turbulences, waves or other disturbances in said sample surface, thus creating an uneven and unstable sample surface, which is undesirable, because the refraction of said probe light beam is therethrough changed, thus altering the measuring conditions. Said first separating member avoids, at least to a great extent, the propagation of such disturbances into said main section of said container. Accordingly, a stable sample surface in such areas, in which said probe light beam and said emitted light (to be detected) penetrates said sample surface, is achieved.

By letting sample liquid flow from said main section to said outlet section (well) below said sample surface, disturbances of said sample surface can be minimized.

In one embodiment, said outlet section comprises an edge to be overflown by excessive sample liquid. Through this edge, a height level of said sample surface is determined, at least in said outlet section and said main section.

In one embodiment, said edge describes a closed shape. That shape may be free from corners. It can be round or elliptic.

Said edge may furthermore be shaped or bent in such a way that, when overflown by sample liquid, the occurrence of turbulences in the outlet section is minimized.

In another embodiment, said container comprises
an inlet section for receiving sample liquid to be measured, having at least one opening to said main section located beneath said sample surface; and
a second separating member for substantially separating a portion of said sample surface belonging to said inlet section from a portion of said sample surface belonging to said main section.

The advantage of this embodiment is similar to the advantage of above-described embodiment with said first separating member. An introduction of (fresh) sample liquid usually leads to some disturbances in said sample surface. By means of said second separating member, it can (largely) be avoided that such disturbances influence the measurement.

The inlet section may also function as a degas section, in which sample fluid can degas, i.e., the degas section is used for the removal of undesired gas solved in the sample fluid, typically just by giving sample fluid some time at the sample surface in the degas unit. The degas unit may also be put under an underpressure so as to enhance the degassing.

In another embodiment, said container comprises a third separating member, by which said sample surface is substantially divided into one partial sample surface, at which said probe light beam is directed, and another partial sample surface, through which said emitted light is emitted generally along said first detection axis. Such a third separating member divides the sample surface in the main section into two parts, which leads to a faster stabilization of the sample surface in the main section, thus allowing for more stable measuring conditions.

In another embodiment, said third separating member comprises said optical barrier.

In another embodiment, said optical barrier extends below said sample surface. It can extend below said sample surface by at least 1 mm or by at least 2 mm or by at least 5 mm or more. This is advantageous, because this way, it can be assured that the optical barrier is always in touch with the sample liquid in the main section. If the optical barrier would extend just to the height level of the sample surface or to just above the height level of the sample surface, small changes in the height level of the sample surface, e.g., due to vibrations or changes in flow velocity, could lead to deformations of the sample surface near the optical barrier due to surface tension effects (capillary forces). This could adversely affect the measurement, at least if the optical barrier is located close to the spot, where the probe light beam enters the sample liquid and/or to the spot, where the emitted light to be detected leaves the sample fluid.

In another embodiment, said optical barrier comprises a beam trap for trapping said light originating from reflection or scattering of said probe light beam at said sample surface propagating generally along said first detection axis. Such a beam trap minimizes reflections of said reflected or scattered probe light from disturbing the detection of said emitted light to be detected.

In another embodiment, said container comprises a beam trap for trapping light of said probe light beam underneath said sample surface. Light of said probe light beam extending beyond the place where said emitted light to be detected originates, can be trapped in said beam trap, so that it does not disturb the measurement. Said beam trap located underneath said sample surface and avoids a further propagation of light not needed for exciting said emitted light to be detected.

In another embodiment, the apparatus comprises a reference detector for obtaining a measure for the intensity of said probe light beam. For calibration purposes and in order to compensate for intensity variations of said light source, the (initial) intensity of said probe light beam can be monitored by said reference detector. Preferably, the intensity of said probe light beam before penetrating said sample surface is monitored.

In another embodiment, the apparatus furthermore comprises a beam splitter for extracting from said probe light beam a reference beam to be detected by said reference detector. By means of said beam splitter, said reference beam can be coupled out of said probe light beam. The intensity of said reference beam is proportional to the intensity of said probe light beam. Such a beam splitter may, e.g., be a plane-parallel plate or just a piece of glass pane, or a prism.

In another embodiment, the apparatus comprises a second light source for generating a second probe light beam directed, in an angle $\beta 2 \neq 0°$ with respect to a surface normal of said sample surface, at said sample surface in a main section of the container. Such a second probe light beam may be used to derive a second value for said property of said sample liquid. In addition, it is possible to derive, with good precision, two properties of said sample liquid, one of them the absorption. The one desired property can be derived with increased accuracy. In one embodiment the two probe light beams describe different optical paths. The two probe light beams may have the same wavelengths or may have different wavelengths. In one embodiment, for the incident angles is valid: $\beta 1 = \beta 2$. In particular, said two probe light beams are parallel to each other. It is possible to have two different light generators, e.g., two lasers, for generating said two probe light beams.

It is also possible to implement said second light source by adding an optical element, e.g., a beam splitter, so as to provide for said two probe light beams, e.g., from one laser or from one light bulb. Detection may be provided for by one detector per probe light beam for detecting scattered light excited by each probe light beam, or by only one detector for detecting scattered light excited by any of said probe light beams.

In one such embodiment, said first detector is adapted to detecting an intensity of emitted light emitted from said sample liquid upon irradiation of said sample liquid with said second probe light beam.

In one embodiment, the apparatus comprises
a second detector for detecting an intensity of said emitted light emitted through said sample surface in said main section out of said sample liquid generally along a second detection axis, said second detection axis forming an angle $\gamma 2 \neq 0°$ with a surface normal of said sample surface.

It may be valid: $\gamma 1 = \gamma 2$. Said second detection axis may be aligned parallel to said first detection axis. Whereas in the embodiment with only one (first) detector and two probe light beams, usually, a variation in time of the intensities of said probe light beams will have to be provided for in order to distinguish detected intensities originating from excitation with said first or said second probe light beam, e.g., by a (mechanical) chopper, this may not be necessary when two detectors are provided and the light paths of said two probe light beams are sufficiently separated from each other. Thus, a continuous excitation and detection may be performed, thus leading to a good signal-to-noise ratio.

In one embodiment, said second detector is adapted to detecting an intensity of emitted light emitted from said sample liquid upon irradiation of said sample liquid with said first probe light beam.

It is also possible to have a setup with a first and a second probe light beam and a first and a second detector.

In general, said at least one property is a physical or chemical property that can be derived from measuring emitted light emitted from said sample liquid upon irradiation of said sample liquid with a probe light beam. Said emitted light is excited by said probe light beam. What is detected, is an excited emission.

In one embodiment, said at least one property comprises at least one of turbidity, absorption, fluorescence, phosphorescence.

In one embodiment, in which at least two light sources are employed and/or in which at least two detectors are employed, said at least one property comprises absorption and at least one of turbidity, fluorescence, phosphorescence.

In one embodiment, within said sample liquid said probe light beam forms an angle $\delta 1$ with $80° \leq \delta 1 \leq 100°$ with said emitted light to be detected by said first detector. In particular, it can be valid $85° \leq \delta 1 \leq 95°$, or more particularly $87.50 \leq \delta 1 \leq 92.5°$. In case that two probe light beams and/or two detectors are employed, the same may hold for the corresponding angles.

Said probe light beam and said first detection axis may be arranged in one plane with a surface normal of said sample surface. In case that two probe light beams and/or two detectors are employed, the same may hold for the corresponding beams or axes. This provides for relatively short path lengths and, accordingly, to higher detected intensities (less scattering and less widening).

In one embodiment applies that $\beta 1 \geq 45°$ or $\beta 1 \geq 60°$ or $\beta 1 = 75° \pm 6°$. The same may apply for $\beta 2$.

In one embodiment applies that $\gamma 1 \geq 35°$ or $\gamma 1 \geq 50°$ or $\gamma 1 = 65° \pm 6°$. The same may apply for $\gamma 2$.

Light paths of probe light beam and emitted light to be detected may be symmetrical or asymmetrical.

In one embodiment, said first detector and, if provided, also said second detector, has an acceptance angle (opening angle of acceptance cone) of $20° \pm 10°$.

In one embodiment, said probe light beam has no divergence.

In one embodiment, said probe light beam has a convergence of at most $3°$, at most $2°$ or at most $1.5°$.

Said probe light beam may be a collimated light beam.

Said light source may comprise a collimator.

Said light source may comprise a laser, in particular a diode laser.

Said light source may comprise a filament or, in particular, a light bulb.

In one embodiment, the light of said probe light beam is infrared light. It may be near-infrared light.

The light of said probe light beam may be visible or invisible light. It may be narrow-frequency light or broad-band. It may be white light.

In one embodiment, said emitted light has a wavelength within 860 nm±30 nm or within 850 nm±10 nm.

In one embodiment, said sample liquid comprises water.

Said sample liquid may be water (an aqueous solution), in particular drinking water.

In one embodiment, the apparatus further comprises a processor programmed to derive said at least property of said sample liquid from said intensity of said emitted light.

Said processor may be programmed to derive at least two properties, in particular an absorption coefficient α (Lambert-Beer coefficient) and, in addition, a turbidity σ (or scattering coefficient σ) or a value for a fluorescence or a value for a phosphorescence.

Usually, the sample surface is an interface between a gas and said sample liquid, in particular the gas being ambient gas, in particular air. The gas could also be a protective gas, e.g., Nitrogen or a noble gas.

Said sample surface can also be a liquid-liquid interface, wherein the second liquid in addition to said sample liquid should be a liquid of lower specific weight than said sample liquid, which does not mix with said sample liquid.

In one embodiment, a bottom outlet for removing sample liquid from said container is foreseen. It may comprise an opening in the bottom of said container. And it may comprise a valve.

The flow cell according to the invention for use with an apparatus for deriving at least one property of a sample liquid from measuring emitted light emitted from said sample liquid upon irradiation of said sample liquid with a probe light beam comprises a container for containing said sample liquid forming a sample surface, and said container comprises a main section, at which said probe light beam is to be directed and through which said emitted light is to be emitted out of said sample liquid for being measured;

an inlet section for receiving sample liquid to be measured, having at least one opening to said main section located beneath said sample surface;

an outlet section for removing sample liquid from said container, having at least one opening to said main section located beneath said sample surface; and an optical barrier arranged in said main section adapted to blocking a propagation of light originating from reflection or scattering of said probe light beam at said sample surface.

The advantages of such a flow cell correspond to the advantages of the corresponding measurement apparatus described above.

In one embodiment, said container furthermore comprises a first separating member for substantially separating a portion of said sample surface belonging to said outlet section from a portion of said sample surface belonging to said main section.

In one embodiment, said container furthermore comprises a second separating member for substantially separating a portion of said sample surface belonging to said inlet section from a portion of said sample surface belonging to said main section.

In one embodiment, said flow cell comprises a holder for a light source.

In one embodiment, said flow cell comprises a holder for a (first) detector.

The method according to the invention for deriving at least one property of a sample liquid comprises the steps of directing a probe light beam at a sample surface formed by said sample liquid in an angle $\beta 1 \neq 0°$ with respect to a surface normal of said sample liquid;

detecting an intensity of emitted light emitted from said sample liquid upon irradiation of said sample liquid with said probe light beam through said sample surface in a main section out of said sample liquid generally along a first detection axis, said first detection axis forming an angle $\gamma 1 \neq 0°$ with a surface normal of said sample surface blocking a propagation of light originating from reflection or scattering of said probe light beam at said sample surface generally along said first detection axis.

The advantages of the methods correspond to the advantages of the corresponding measurement apparatuses described above.

In one embodiment, the method furthermore comprises the steps of receiving in an outlet section sample liquid from said main section through at least one opening located beneath said sample surface;

removing sample liquid out of said outlet section from said container;

substantially separating a portion of said sample surface belonging to said outlet section from a portion of said sample surface belonging to said main section.

Sample liquid to be removed from said container is contained in said outlet section.

In one embodiment, the method furthermore comprises the steps of introducing sample liquid to be measured into said container in an inlet section;

receiving in said main section sample liquid from said inlet section through at least one opening located beneath said sample surface;

substantially separating a portion of said sample surface belonging to said inlet section from a portion of said sample surface belonging to said main section. Said inlet section is to receive new (fresh) sample liquid. In said inlet section sample liquid is received from out of the container.

In one embodiment, the method furthermore comprises the step of substantially dividing said sample surface into one partial sample surface, at which said probe light beam is directed, and another partial sample surface, through which said emitted light is emitted generally along said first detection axis.

By means of the invention it is possible to measure with a fast response time, since it is possible to have a small volume for containing sample liquid to be analyzed.

Further preferred embodiments and advantages emerge from the dependent claims and the figures.

BRIEF DESCRIPTION OF THE DRAWINGS

Below, the invention is described in more detail by means of examples and the included drawings. The figures show:

FIG. 3 a detail of a cross-section of the apparatus of

FIG. 1 along the plane indicated as III-III in FIG. 2, partially diagrammatic;

The reference symbols used in the figures and their meaning are summarized in the list of reference symbols. Generally, alike or alike-functioning parts are given the same or similar reference symbols. The described embodiments are meant as examples and shall not confine the invention.

DETAILED DESCRIPTION OF THE INVENTION

Figure 1:
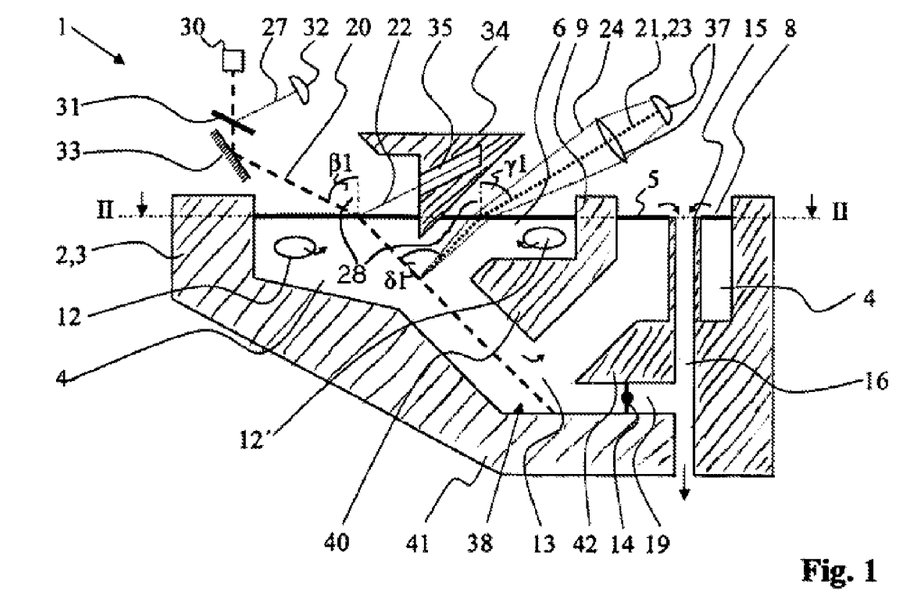
FIG. 1 a cross-section of an apparatus according to the invention along the plane indicated as I-I in FIG. 2, partially diagrammatic.

FIG. 1 shows a cross-section of an apparatus 1 according to the invention. A flow cell 2 comprises a container 3 containing a sample fluid 4. A light source 30, e.g. a diode laser, generates light, which impinges on a beam splitter 31 thus generating a reference beam 27 to be detected by a reference detector 32. Light generated by said light source 30 is reflected by a mirror 33 and forms a probe light beam 20. Said probe light beam 20 impinges on the sample surface 5 of the sample fluid 4 with an incidence angle β1 with respect to the surface normal 28 which is indicated by a thin dashed-dotted line. Some of the intensity of the probe light beam 20 is reflected at the sample surface 5 forming a reflected beam 22 and scattered light, the latter not indicated in FIG. 1. An optical barrier 34 provides for a beam trap 35, which absorbs said reflected beam 22. A large portion of the probe light beam 20 is refracted at sample surface 5 and enters the sample liquid 4.

Within the sample liquid 4 the probe light beam 20 excites emitted light 21. In case that the apparatus 1 is a turbidimeter 1, the emitted light 21 is light scattered from particles within the sample fluid 4. If the apparatus 1 is a fluorescence meter 1, the emitted light 21 is fluorescence light excited by the probe beam 20. If the apparatus 1 is an apparatus for measuring phosphorescence, the emitted light 21 is phosphorescence light excited by the probe light beam 20. A part of the emitted light 21 propagates towards the sample surface 5 and is refracted when exiting the sample fluid 4.

Outside the sample fluid 4 the emitted light 21, which is to be detected, forms an angle γ1 with the surface normal 28 of the sample surface 5. Within the sample fluid 4 the refracted probe light beam forms an angle δ1 with the emitted light 21 to be detected by detector 37. The surface normal 28 is indicated as a thin dashed-dotted line. A detector 37 comprising a photo cell and a lens detects the emitted light 21. The detector 37 detects light emitted generally along a detection axis 23. Light within a detection cone 24 can be detected by detector 37. The intensity of the detected light is at 5 least in a first approximation proportional to the amount of fluorescence, phosphorescence and scattering, respectively, within the sample fluid 4. Thus, the detected intensity is closely related to the amount of fluorescent material, phosphorescent material and scattering particles, 10 respectively, contained in the sample fluid 4.

The incidence of probe light beam 20 on the sample surface 5 and the emission of emitted light 21 to be detected by the detector 37 out of the sample fluid takes place in a main section 6 of the container 3. A third separating member 11 divides the sample surface 5 within the main section 6 into, one partial sample surface, at which the probe light beam is directed, and another partial sample surface through which said emitted light is emitted generally along said first detection axis. The function of the third separation member 11 can also be satisfied. The optical barrier 34, functions to block the light originating from reflection or scattering of the probe light beam. However, in the embodiments shown in FIGS. 2, 4 and 5 it takes on a dual role and also performs the function of the third separating member 11 which, as mentioned above, is to substantially divide the sample surface 5.

Figure 2:
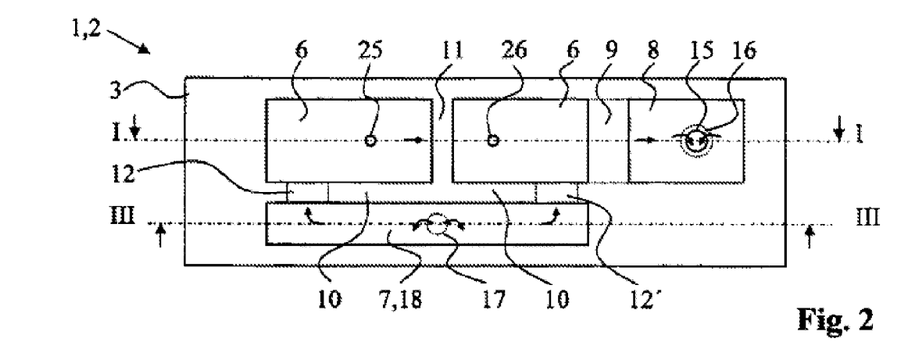
FIG. 2 a top-view onto a cross-section of the apparatus of FIG. 1, the cross-section running along the plane indicated as II-II in FIGS. 1 and 3.
Figure 3:
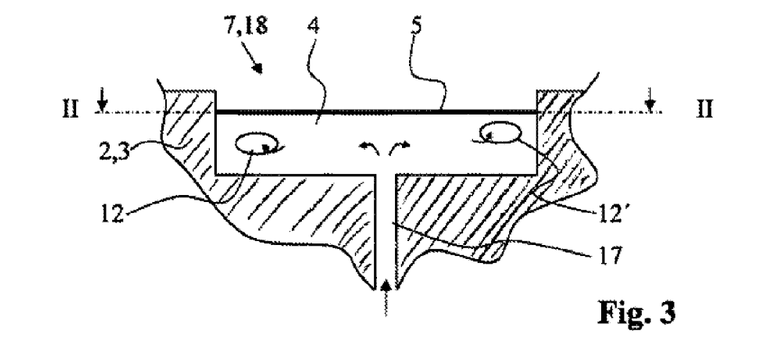

FIG. 2 shows a top view onto a cross-section of the apparatus 1 of FIG. 1, the cross-section running along the plane indicated as II-II in FIGS. 1 and 3. In addition to the main section 6, the container 3 comprises an inlet section 7 and an outlet section 8. Fresh sample fluid 4 is received through an inlet tube 17 within the inlet section 7. Inlet section 7 functions at the same time as a degas section 18. During the time when sample fluid 4 is located in the degas section 18, gas which is possibly solved in the sample fluid 4 may exit the sample fluid through the sample surface 5. In addition, contaminations and particles possibly carried in the sample liquid 4 can sediment in the inlet section 7 or swim on the sample surface in the inlet section 7. A transport of such contaminations and particles into the main section 6 is inhibited, in particular since openings 12 and 12', through which sample fluid 4 flows from the inlet section 7 into the main section 6, are located above the bottom of the container 3 in the inlet section 7 and below the sample surface 5 (in the inlet section 7). Instead of two openings 12, 12', there could also be only one opening or a larger number of openings.

The spot 25, where the probe light beam 20 penetrates the sample surface 5, and the spot 26, where emitted light to be detected by the detector 37 penetrates the sample surface 5, are indicated. From the main section 6 the sample fluid 4 flows to the outlet section 8 through an opening 13 (see also FIG. 1). The outlet section 8 comprises an outlet tube 16 having an edge 15, which is overflown by sample fluid 4. Accordingly, the edge 15 determines the height level of the sample surface 5 within the container. Sample fluid 4 after flowing over the edge 15 exits the container through the outlet tube 16.

A first separating member 9 separates the main section 6 from the outlet section 8. A second separating member 10 separates the main section 6 from the inlet section 7. The cross-section shown in FIG. 1 runs along the dashed dotted line indicated by II-II in FIG. 2. In FIGS. 1, 2 and 3 the directions of the flow of sample liquid are indicated by small arrows.

As indicated in FIG. 1, a beam trap 38 is comprised in the container 3 for trapping that portion of the light of the probe light beam 20, which extends beyond the point where the emitted light 21 to be detected originates. The beam trap 38 comprises a member 40, which is integrally formed with the first separating member 9, a member 41 and a member 42. On the bottom of the main section 6 a flushing opening 19 is provided, in which a valve 14 is arranged, by means of which the connection 19 between the main section 6 and the outlet tube 16 can be opened or closed. Solid material possibly contained in the sample fluid 4, which would sediment on the bottom of the container 3 and possibly disturb the measurement when whirled up, can be removed from the container 3 by flushing the container with the valve 14 open. And also material possibly contained in the sample fluid 4, which would swim on the sample surface 5, in particular in the main section 6, can be removed from the container 3 by flushing the container with the valve 14 open.

FIG. 3 shows a detail of a cross section of the apparatus 1 of FIG. 1 along the plane indicated as III-III in FIG. 2. The inlet tube 17 and the two openings 12 and 12', as well as the directions of sample fluid flow are indicated in FIG. 3.

Figure 4:
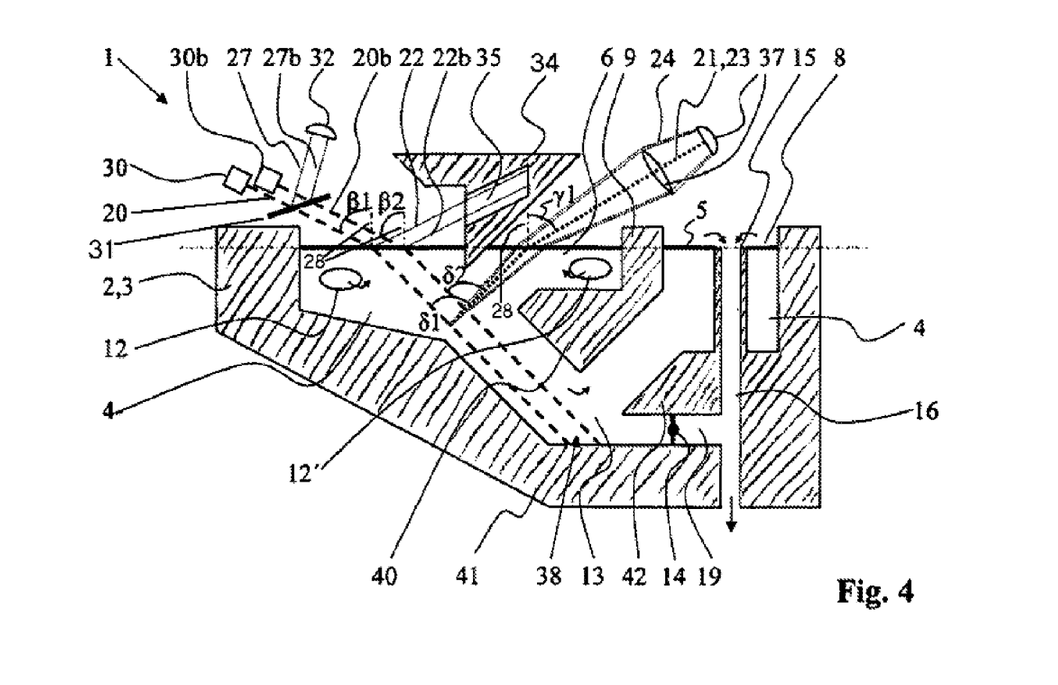
FIG. 4 a cross-section of an apparatus with two light sources, partially diagrammatic.

FIG. 4 shows another apparatus 1. As far as the container 3 is concerned, this apparatus 1 is substantially identical with the apparatus shown in FIGS. 1 to 3. But the optical setup is different from FIGS. 1 to 3. The apparatus 1 of FIG. 4 comprises two light sources 30 and 30b, which generate two probe light beams 20 and 20b, respectively. A beam splitter 31 extracts two reference beams 27 and 27b from the probe light beams 20 and 20b, which reference beams are detected by reference detector 32. The probe light beams 20, 20b impinge on the sample surface 5 under angles β1 and β2, respectively, with the surface normal 28. Light reflected or scattered at the sample surface 5 is blocked by the optical barrier 34, which prevents light from the probe light beam 20 which is scattered at the sample surface 5 from being detected by the detector 37. In particular, reflected beams 22 and 22b are trapped in the beam trap 35 of the optical barrier 34. Within the sample fluid, emitted light is generated which, when refracted upon leaving the sample fluid, propagates along the detection direction 21, forming an angle γ1 with the surface normal 28 of the sample surface. Within the sample the probe light beams 20 and 20b, respectively, form angles δ1 and δ2, respectively, with the emitted light. In the embodiment of FIG. 4, both angles δ1 and δ2 are approximately 90°. Incident angles β1 and β2 20 are chosen substantially equal.

Due to the use of two light sources 30 and 30b it is possible to determine not only one, but two properties of the sample liquid 4. The length of the light path within the sample fluid 4 is different for the first probe light beam 20 and the second probe light beam 20b. Therefore, a value for the turbidity, the fluorescence or the phosphorescence can be corrected for absorption within the sample liquid 4, and an absorption coefficient can be determined. In order to distinguish between light emitted upon excitation with the first probe light beam 20 and light emitted upon excitation with the second probe light beam 20b, the light sources 30 and 30b can be switched on and off alternatively, e.g., by means of a chopper.

It is possible to implement a second light source for generating a second probe light beam by using one single light generator (laser, bulb . . . ) plus another optical element, e.g., a mirror or a beam splitter.

Figure 5:
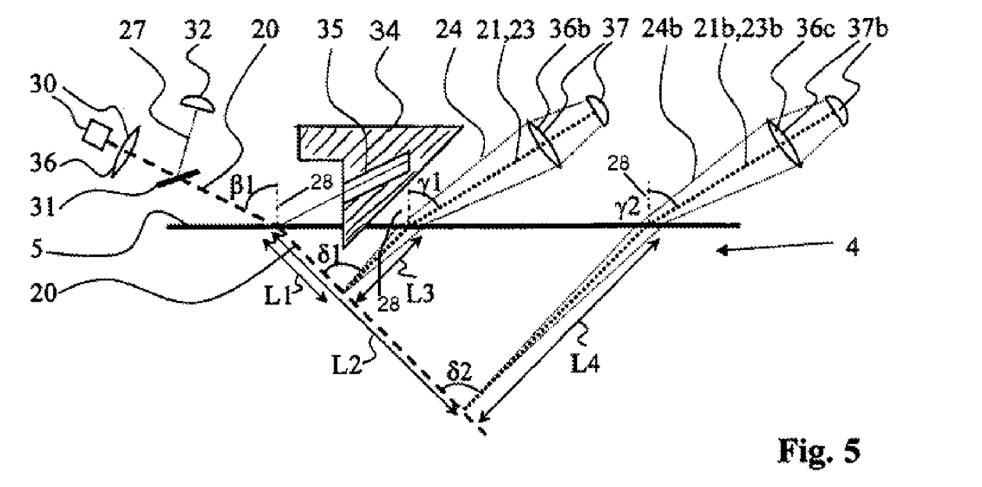
FIG. 5 a sketch of the light paths in an embodiment with one light source and two detectors.

FIG. 5 shows another embodiment, but with most details of the container not shown. This embodiment is similar to the embodiments of the FIGS. 1 to 4, but it comprises one light source 30 and two detectors 37 and 37b. It is possible to implement a second detector in form of one single photo-sensitive element (e.g., photo cell) plus another optical element, e.g., a mirror or a beam splitter. The light source 30 comprises a collimator lens 36. As shown in FIG. 5, the angles 61 and 62 can be chosen as δ1=δ2, and the angles γ1 and γ2 may be chosen as γ1=γ2.

Up to the point, from which emitted light 21 to be detected by the detector 37 is emitted, the probe light beam 20 travels within the sample liquid 4 by a length L1. The emitted light 21 itself travels by a length of L3 within the sample fluid 4. The lengths L1 und L3 are shorter than the corresponding lengths L2 and L4 occuring in conjunction with light finally to be detected by the second detector 37b. Using the Lambert-Beer equation, the absorption of light within the sample fluid 4 can be calculated separately from the intensity of the generation of emitted light (scattered light; fluorescence light; phosphorescence light). By means of an apparatus with more than one detector, e.g., like shown in FIG. 5, is possible to derive the absorption and turbidity independently from fluorescence or phosphorescence by employing wavelength-selective detectors. For example, a color filter may be placed in the light path before the detector.

A processor can be used for calculating the desired properties of the sample liquid 4 from the detected intensities.

Figure 6:
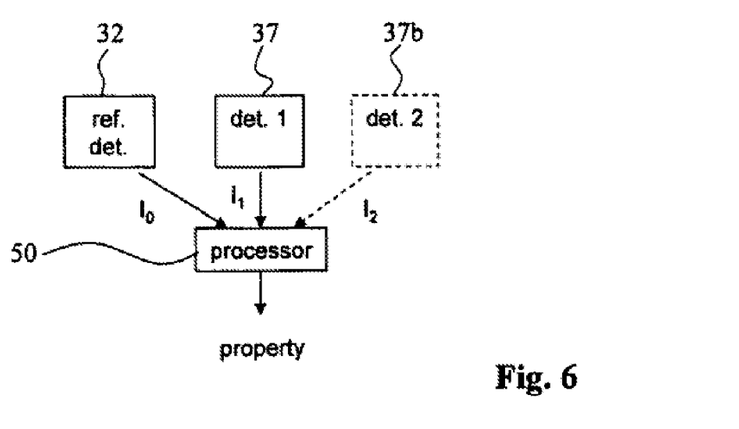
FIG. 6 a diagram describing input to a processor and output of the processor.

FIG. 6 shows a diagram describing input to processor 50 and output of processor 50. Processor 50 receives a reference intensity $I_0$ from the reference detector 32, an intensity $I_1$ from detector 37 and, if available, an intensity $I_2$ from detector 37b. If, like in FIG. 4, two light sources are employed, two reference intensities can be fed to processor 50. The intensities input to processor 50 are used in formulas within the processor, and the at least one property of the sample liquid is readily calculated. Intensities measured with known sample liquids may be used as gauge measurements.

In case of turbidity- and absorption-measurements with an apparatus like shown in FIG. 5, with δ1=δ2=90°, values for an absorption coefficient α of the sample liquid 4, an integral scattering coefficient σ of the sample liquid 4, and a scattering coefficient $\sigma_{90}$ in 90° to the beam of the sample liquid 4 can be obtained in a straight-forward manner, e.g., along the following lines:

$I_1 = \sigma_{90} I_0 \exp[-(\alpha+\sigma)(L1+L3)]$ $I_2 = \sigma_{90} I_0 \exp[-(\alpha+\sigma)(L2+L4)]$ $(\alpha+\sigma) = -\ln(I_1/I_2)/(L1+L3-L2-L4)$ $\sigma_{90} = I_1/I_0 \ast \exp[(\alpha+\sigma)(L1+L3)]$, and $\sigma_{90} = I_2/I_0 \ast \exp[(\alpha+\sigma)(L1+L3)]$, with $I_0$=initial intensity, $I_1$=intensity at first detector, I2=intensity at second detector, and L1, L2, L3, L4 optical path lengths as indicated in FIG. 5.

For even more precise results, it is possible to operate with more refined formulas. The case of two light sources and one detector like, e.g., shown in FIG. 4, and the case of only one light source and only one detector like, e.g., shown in FIGS. 1-3, can be derived analogously. In case of fluorescence and phosphorescence measurements, corresponding equations can be derived analogously.

Typical dimensions of the apparatus are: volume of contained sample liquid: of the order of 100 ml to 500 ml, can be below 50 ml or below 20 ml, but typically above 10 ml; flow rate of sample liquid within the container 1 ml/s to 10 ml/s, can be as low as 0.2 ml/s±0.1 ml/s.

By means of the separating members 9,10,11 of FIGS. 2 and 4, it is possible to assure a very calm and flat sample surface 5 in the main section 6. The fact that the openings 12,12',13 connecting the sections 6,7,8 of the container are arranged below the sample surface 5 also supports the formation of a stable sample surface in the main section 6.

For fluorescence and phosphorescence measurements the wavelength(s) of the light source has to be chosen suitably.

$I_0$ initial intensity, intensity of probe light beam
$I_1$ intensity of emitted light (detected in first detector)
$I_2$ intensity of emitted light (detected in second detector)
L1,L2,L3,L4 lengths, optical path lengths
α absorption coefficient
β1 incident angle, angle of incidence of (first) probe light beam, measured against surface normal
β2 incident angle, angle of incidence of second probe light beam, measured against surface normal
γ1 angle of (first) detection axis measured against surface normal
γ2 angle of second detection axis measured against surface normal
δ1 angle between refracted (first) probe light beam and emitted light to be detected, within the sample liquid
δ2 angle between refracted second probe light beam and emitted light to be detected, within the sample liquid
σ scattering coefficient (integral)
$\sigma_{90}$ scattering coefficient for 90°-scattering

The invention claimed is:
1. Apparatus for deriving at least one property of a sample liquid from measuring emitted light emitted from said sample liquid upon irradiation of said sample liquid with a probe light beam, said apparatus having a preselected plane and an operable state in which the apparatus contains said sample liquid and is aligned such that a sample surface formed by said sample liquid is at least substantially horizontal and substantially coincides with said preselected plane, said apparatus comprising:
- a container adapted for containing said sample liquid and comprising
  - a main section containing, when in said operable state, at least a portion of said sample liquid, and
  - a beam trap located and arranged, when in said operable state, below said preselected plane and adapted for trapping light of said probe light beam underneath said preselected plane; and
- each arranged in a defined position relative to said container:
  - a light source adapted and arranged for generating said probe light beam to be directed, when in said operable state, from above said preselected plane in an angle $\beta 1 \neq 0°$ with respect to a surface normal of said preselected plane, along a path at said sample surface in said main section of said container;
  - a first detector adapted to detect, when in said operable state, an intensity of said emitted light emitted out of said sample liquid through said sample surface in said main section generally along a first detection axis, said first detection axis forming an angle $\gamma 1 \neq 0°$ with a surface normal of said preselected plane; and
  - an optical barrier arranged between a spot at which, when in said operable state, the path of said probe light beam and said preselected plane intersect, and a spot at which, when in said operable state, said first detection axis and said preselected plane intersect, and adapted to block, when in said operable state, a propagation of light originating from reflection or scattering of said probe light beam at said sample surface towards and into said first detector.

2. Apparatus according to claim 1, said container comprising:
- an outlet section not identical with said main section and containing, when in said operable state, at least a portion of said sample liquid, for removing, when in said operable state, sample liquid from said container and having at least one opening to said main section located beneath said sample surface; and
- a first separating member positioned between said outlet section and said main section and substantially separating, when in said operable state, a portion of said sample surface belonging to said outlet section from a portion of said sample surface belonging to said main section.

3. Apparatus according to claim 2, said outlet section comprising an overflow edge to be overflown, when in said operable state by excessive sample liquid, said overflow edge being located at said selected plane.

4. Apparatus according to claim 3, said overflow edge describing a closed shape.

5. Apparatus according to claim 1, wherein said container comprises:
- an inlet section not identical with said main section and containing, when in said operable state, at least a portion of said sample liquid, adapted for receiving sample liquid to be measured, having at least one opening to said main section located beneath said sample surface; and
- a second separating member positioned between said inlet section and said main section and substantially separating, when in said operable state, a portion of said sample surface belonging to said inlet section from a portion of said sample surface belonging to said main section.

6. Apparatus according to claim 1, said container comprising within said main section a third separating member by means of which, when in said operable state, a portion of said sample surface belonging to said main section is substantially divided into one partial sample surface, comprising a spot at which, when in said operable state, the path of said probe light beam and said preselected plane intersect, and another partial sample surface comprising a spot at which, when in said operable state, said first detection axis and said preselected plane intersect.

7. Apparatus according to claim 6, wherein said third separating member and said optical barrier are realized in one element.

8. Apparatus according to claim 1, wherein said optical barrier extends across said preselected plane.

9. Apparatus according to claim 1, said optical barrier comprising a beam trap for trapping, when in said operable state, said light originating from reflection or scattering of said probe light beam at said sample surface propagating towards and into said first detector.

10. Apparatus according to claim 1, comprising a reference detector adapted and arranged in a defined position relative to said container for obtaining a measure for the intensity of said probe light beam.

11. Apparatus according to claim 10, further comprising a beam splitter arranged in a defined position relative to said container and, when in said operable state, in the path of said probe light beam and adapted for extracting, when in said operable state, from said probe light beam a reference beam to be detected by said reference detector, said reference detector being adapted and arranged for detecting, when in said operable state, said reference beam, said measure for said intensity of said probe light beam being derived from the result of said detection of said reference beam.

12. Apparatus according to claim 1, comprising a second light source adapted and arranged in a defined position relative to said container for generating a second probe light beam to be directed, when in said operable state, from above said preselected plane, in an angle $\beta 2 \neq 0°$ with respect to a surface normal of said preselected plane at said sample surface in said main section of the container.

13. Apparatus according to claim 12, wherein said first detector is adapted to detect, when in said operable state, an intensity of emitted light emitted from said sample liquid upon irradiation of said sample liquid with said second probe light beam.

14. Apparatus according to claim 1, comprising: a second detector positioned in a defined position relative to said container and adapted to detect, when in said operable state, an intensity of said emitted light emitted out of said sample liquid through said sample surface in said main section generally along a second detection axis, said second detection axis forming an angle $\gamma 2 \neq 0°$ with a surface normal of said preselected plane.

15. Apparatus according to claim 14, wherein said second detector is adapted and arranged for detecting, when in said operable state an intensity of emitted light emitted from said sample liquid upon irradiation of said sample liquid with said first probe light beam.

16. Apparatus according to claim 1, said at least one property comprising at least one of turbidity, fluorescence, and phosphorescence.

17. Apparatus according to claim 12, said at least one property comprising absorption and at least one of turbidity, fluorescence, and phosphorescence.

18. Apparatus according to claim 14, said at least one property comprising absorption and at least one of turbidity, fluorescence, and phosphorescence.

19. Apparatus according to claim 1, wherein, when in said operable state, said probe light beam forms within said sample liquid an angle δ with 80°≦δ≦100° with said emitted light to be detected by said first detector.

20. Apparatus according to claim 1, wherein said light source is a light source for generating a light beam having no divergence.

21. Apparatus according to claim 1, wherein said light source is an infrared light source generating an infrared probe light beam.

22. Apparatus according to claim 1, being adapted for deriving, from measuring emitted light emitted from said sample liquid upon irradiation of said sample liquid with a probe light beam, at least one property of a sample liquid comprising water.

23. Apparatus according to claim 1, further comprising a processor programmed to derive said at least one property of said sample liquid from said intensity of said emitted light detected, when in said operable state.

24. Method for deriving at least one property of a sample liquid comprising the steps of
- providing in a container a sample liquid having an at least substantially horizontally aligned sample surface;
- generating a probe light beam;
- directing, from above, said probe light beam along a path at said sample surface in a direction forming an angle $\beta \neq 0°$ with respect to a surface normal of said sample liquid;
- detecting an intensity of emitted light emitted upon irradiation of said sample liquid with said probe light beam from said sample liquid and
  - through said sample surface in a main section of said container and
  - out of said sample liquid generally along a first detection axis, said first detection axis forming an angle $\gamma 1 \neq 0°$ with a surface normal of said sample surface,
- by means of a detector detecting an intensity of light propagating above said sample surface along said first detection axis;
- blocking a propagation of light originating from reflection or scattering of said probe light beam at said sample surface towards and into said detector;
- trapping light of said probe light beam underneath said sample surface by means of a beam trap located underneath said sample surface.

25. Method according to claim 24, furthermore comprising the steps of:
- using a container comprising an outlet section and a first separating member positioned between said outlet section and said main section and substantially separating a portion of said sample surface belonging to said outlet section from a portion of said sample surface belonging to said main section;
- receiving in said outlet section sample liquid from said main section through at least one opening located beneath said sample surface; and
- removing sample liquid out of said outlet section from said container.

26. Method according to claim 24, furthermore comprising the steps of:
- using a container comprising an inlet section and a second separating member positioned between said inlet section and said main section and substantially separating a portion of said sample surface belonging to said inlet section from a portion of said sample surface belonging to said main section;
- introducing sample liquid to be measured in said container into said inlet section;
- receiving in said main section sample liquid from said inlet section through at least one opening located beneath said sample surface.

27. Method according to claim 24, further comprising the step of:
- using a container comprising a third separating member positioned in said main section and substantially dividing a portion of said sample surface belonging to said main section into one partial sample surface comprising a snot at which the path said probe light beam and said sample surface intersect, and another partial sample surface comprising a spot at which said first detection axis and said sample surface intersect.

28. Apparatus according to claim 3, said outlet section comprising an outlet tube, said overflow edge forming an open top of said outlet tube.

29. Apparatus for deriving at least one property of a sample liquid from measuring emitted light emitted from said sample liquid upon irradiation of said sample liquid with a probe light beam, said apparatus comprising:
- said sample liquid;
- a container containing said sample liquid, said sample liquid forming a sample surface therein, said container comprising
  - a main section containing at least a portion of said sample liquid, and
  - a beam trap located and arranged below said sample surface and adapted for trapping light of said probe light beam underneath said sample surface; and
- each arranged in a defined position relative to said container:
- a light source adapted and arranged for generating said probe light beam to be directed, in an angle $\beta 1 \neq 0°$ with respect to a surface normal of said sample surface, along a path at said sample surface in said main section of said container;
- a first detector adapted to detect an intensity of said emitted light emitted out of said sample liquid through said sample surface in said main section generally along a first detection axis, said first detection axis forming an angle $\gamma 1 \neq 0°$ with a surface normal of said sample surface; and
- an optical barrier arranged between a spot at which the path of said probe light beam and said sample surface intersect, and a spot at which said first detection axis and said sample surface intersect, and adapted to block a propagation of light originating from reflection or scattering of said probe light beam at said sample surface towards and into said first detector.

* * * * *